(12) United States Patent
Pfeifer et al.

(10) Patent No.: US 9,188,526 B2
(45) Date of Patent: Nov. 17, 2015

(54) DEVICE FOR PHOTOMETRIC ANALYSIS OF A LIQUID SAMPLE AND SAMPLE CARRIER THEREFOR

(71) Applicant: Berthold Detection Systems GmbH, Pforzheim (DE)

(72) Inventors: Lutz Pfeifer, Hennigsdorf (DE); Karsten Stein, Berlin (DE); Berthold Breitkopf, Straubenhardt (DE)

(73) Assignee: Berthold Detection Systems GmbH, Pforzheim (DE)

( * ) Notice: Subject to any disclaimer, the term of this patent is extended or adjusted under 35 U.S.C. 154(b) by 347 days.

(21) Appl. No.: 13/859,597

(22) Filed: Apr. 9, 2013

(65) Prior Publication Data

US 2013/0228710 A1    Sep. 5, 2013

Related U.S. Application Data

(63) Continuation of application No. PCT/EP2011/004641, filed on Sep. 15, 2011.

(51) Int. Cl.
*G01N 21/17* (2006.01)
*G01N 21/03* (2006.01)
*G01N 21/59* (2006.01)

(52) U.S. Cl.
CPC .............. *G01N 21/17* (2013.01); *G01N 21/031* (2013.01); *G01N 21/59* (2013.01); *G01N 2021/035* (2013.01)

(58) Field of Classification Search
CPC ..... G01N 21/17; G01N 21/031; G01N 21/59; G01N 2021/035
USPC .......................................... 250/576; 356/440
See application file for complete search history.

(56) References Cited

U.S. PATENT DOCUMENTS

| 5,311,283 | A  * | 5/1994  | Heeschen ..................... 356/364 |
| 6,817,754 | B2   | 11/2004 | Tsang et al. |
| 7,483,138 | B2   | 1/2009  | Sahiri et al. |
| 7,688,429 | B2   | 3/2010  | Sahari et al. |
| 2002/0024018 | A1 * | 2/2002 | Saito et al. ................. 250/458.1 |
| 2008/0253933 | A1 | 10/2008 | Redfern |

FOREIGN PATENT DOCUMENTS

| DE | 102 22 785 A1     | 12/2003 |
| DE | 10 2004 023 178 A1 | 12/2005 |
| DE | 10 2004 039 564 A1 | 3/2006  |
| DE | 10 2005 036 898 A1 | 2/2007  |
| JP |       2-236147    | 9/1990  |
| WO | WO 2008/112856 A1 | 9/2008  |

* cited by examiner

*Primary Examiner* — Seung C Sohn
(74) *Attorney, Agent, or Firm* — Bose McKinney & Evans LLP

(57) ABSTRACT

The invention relates to a device for the analysis of a liquid sample by way of light, comprising a transparent sample carrier, a movable upper mirror, which can be moved between a closed position, in which the mirror encloses a measurement space between itself and the sample carrier, and an open position, in which the sample carrier can be accessed so as to apply a sample, and a beam path, which guides incident measurement light between a light entrance into the measurement space and a light exit out of the measurement space from the sample carrier to the upper mirror reflecting the light. The beam path guides measurement light at an oblique angle of incidence through the sample carrier to the upper mirror.

15 Claims, 4 Drawing Sheets

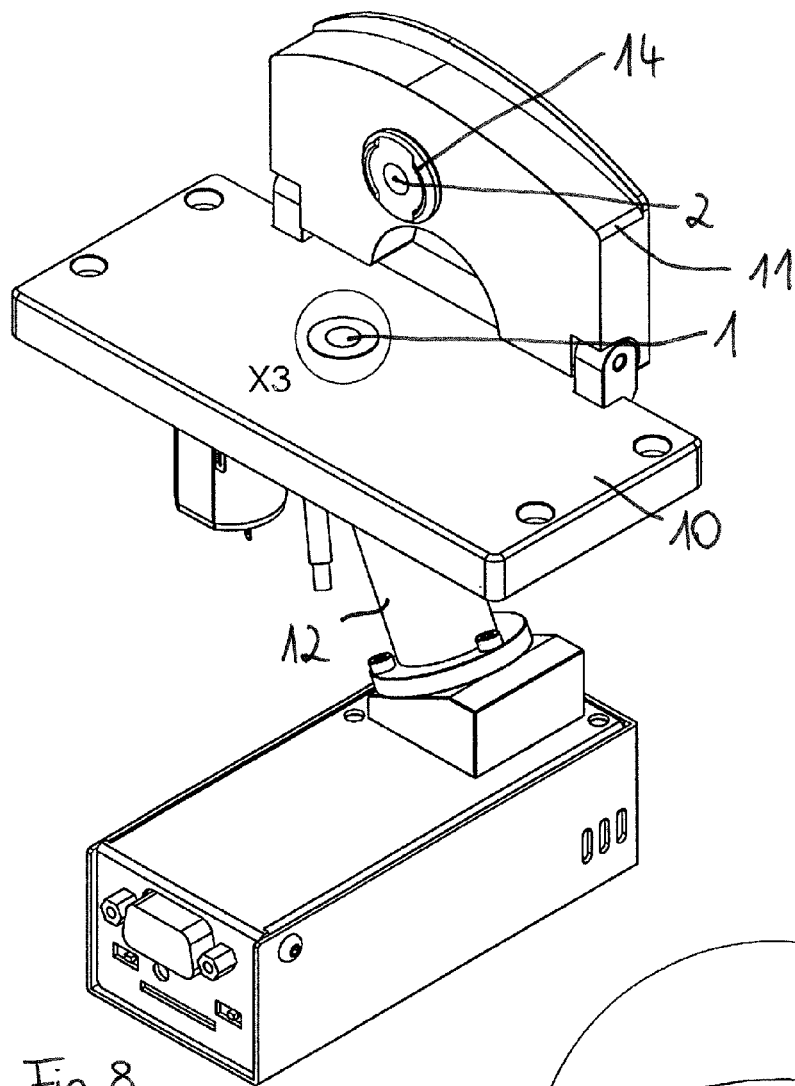
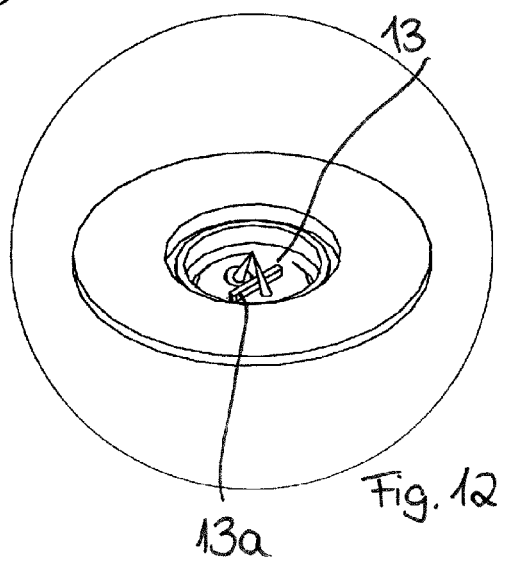

DEVICE FOR PHOTOMETRIC ANALYSIS OF A LIQUID SAMPLE AND SAMPLE CARRIER THEREFOR

RELATED APPLICATIONS

This application is a continuation of PCT/EP2011/004641, filed Sep. 15, 2011, which claims priority to DE 10 2010 048 651.5, filed Oct. 15, 2010, both of which are hereby incorporated by reference in their entirety.

BACKGROUND

The invention relates to a device for the photometric, in particular spectral photometric, analysis of a liquid sample having the characteristics described in the preamble of claim 1.

Such a device is known from DE 10 2004 023 178 B4. In the known device, a liquid sample is enclosed in a measurement space between a transparent sample carrier and an upper mirror located parallel thereto. Measurement light is radiated through the transparent sample carrier perpendicularly onto the upper mirror so as to analyze the sample. The upper mirror reflects the measurement light beam, so that the measurement light beam passes through the measurement space a total of two times between the light entrance and light exit.

A common method for analyzing liquid samples by way of light is the measurement of the sample absorption at one or more characteristic wavelengths. To this end, an absorption spectrum is generally measured, so as to detect analytes in a sample and determine the concentrations thereof. The level of absorption is the product of the optical path length of the measurement light through the sample, the analyte concentration and an extinction coefficient that is characteristic of the analyte in question at the respective light wavelength. For known extinction coefficients, it is thus possible to calculate a required analyte concentration based on the measured absorption values.

When liquid biological or biochemical samples are analyzed, for example for the quantitative determination of different nucleic acids, proteins or marker dyes, the problem arises that generally only small amounts of samples are available and therefore a quantitative analysis is made difficult.

SUMMARY

The present invention provides a means for small liquid samples, in particular a single drop, to be better analyzed by way of light. According to this disclosure, measurement light is irradiated obliquely through a measurement space onto an upper mirror, where the light is reflected. A larger path length through a sample that is present in the measurement space is thus achieved.

According to this disclosure, it can be achieved that the beam cross-sections of measurement light that enters the measurement space for the first time through the sample carrier and is reflected by the upper mirror do not overlap. With a device according to this disclosure, it is thus possible for measurement light coming from the upper mirror to be reflected by a lower mirror and thus achieve a further increase in the path length of a measurement light beam through a sample to be analyzed. Because the beam path of a device according to this disclosure guides measurement light at an oblique angle of incidence through the sample carrier to the upper mirror, measurement light impinges on the upper mirror at an oblique angle and is reflected accordingly obliquely. A measurement light beam can thus be reflected by the upper mirror to a lower mirror that is arranged laterally of the light entrance. The measurement light beam then impinges on the lower mirror at an oblique angle and is reflected back up by the lower mirror. There, the light beam can again be reflected by the upper mirror.

Because of the oblique incidence of light, the light beam is deflected slightly to the side during each reflection, and in particular more strongly so, the flatter the incident light is. This lateral migration of the light beam through the measurement space causes the measurement light beam to finally exit the measurement space past the lower mirror or the upper mirror and to be supplied to a detector. Preferably both the light exit from the measurement space and the light entrance take place through the transparent sample carrier. However, it is also possible in general for the light exit from the measurement space to take place in an upward direction, in that a measurement light beam is guided past the upper mirror after having been reflected once or several times by the lower mirror.

By obliquely reflecting a light beam at the upper mirror and the lower mirror, measurement light can thus be guided through the measurement space not only twice, but also significantly more often. A greater number of passes of a measurement light beam through the measurement space allows a very large optical path length, and thus high measurement accuracy, to be achieved, even if the sample volumes are very small.

The angle at which a measurement light beam obliquely impinges on the upper mirror can be selected relatively freely within a broad range. It is particularly advantageous if the measurement light beam includes an angle of 10° or more, in particular at least 20°, with a straight line that extend perpendicularly relative to the upper mirror. However, the angle is preferably not greater than 45°.

According to an advantageous refinement of this disclosure, the lower mirror can be moved. The number of passes of a measurement light beam through the measurement space can thus be adjusted to the requirements of a particular sample. The lower mirror can preferably be moved between a first and a second position, wherein the lower mirror brings about a larger number of passes of the measurement light beam through the measurement space in the first position than in the second position.

For example, the lower mirror can be inactive in the second position. This means that a measurement light beam coming from the upper mirror is not reflected by the lower mirror and directly reaches the light exit out of the measurement. In this case, a measurement light beam thus exits the measurement space after only two passes. In contrast, if the lower mirror is in the first position thereof, a measurement light beam coming from the upper mirror is reflected at least once, resulting in a larger number of passes of the measurement light beam through the measurement space.

In the first position, the lower mirror is preferably located between the light entrance and the light exit. The number of reflections, and consequently the number of passes of a measurement light beam through the measurement space, are then dependent on the size of the lower mirror. When a small lower mirror is used, for example, a measurement light beam is reflected only once by the lower mirror and can then exit the measurement space laterally past the lower mirror, after the beam was reflected only twice by the upper mirror. In contrast, the measurement light beam is reflected twice, three times or even more often than that by the lower mirror before exiting the measurement space if an accordingly larger lower mirror is used.

The lower mirror can be held in the device so as to be rotatably movable. However, it is also possible to arrange the lower mirror displaceably in the device. Preferably several lower mirrors are present. It is thus possible to implement three or even more different numbers of passes of a measurement light beam through the sample.

According to a further advantageous refinement of this disclosure, the lower mirror is designed as a mirrored sub-area of the sample carrier. The lower mirror can thus advantageously be integrated in the sample carrier, so that the device according to this disclosure is simpler to mount. However, it is also possible in general to design the sample carrier and lower mirror as separate components that can be moved relative to one another. It is particularly preferred to arrange the mirrored part of the carrier area on the lower face of the sample carrier. It is then possible to avoid contact of a liquid sample to be analyzed with the mirrored sub-area. This is advantageous because a metal film that is applied onto the sample carrier for mirroring could chemically react with the liquid sample upon contact, or could catalyze. Preferably several sub-areas on the lower face of the sample carrier are mirrored, so as to create several different lower mirrors. The different lower mirrors can be used selectively so as to implement beam paths with different numbers of passes through the sample.

According to a further advantageous refinement of this disclosure, the height of the sample carrier can be adjusted with respect to the upper mirror. The distance between the sample carrier and the upper mirror can thus be adjusted to an advantageous value for a particular sample. A height adjustment will also change the path length traveled during a pass of a measurement light beam through the measurement space. By being able to adjust both the lengths of the individual passes and the number of passes in accordance with the requirements of a sample to be analyzed, very high variability is provided.

One aspect of the disclosure relates also to a sample carrier which comprises a lower mirror, which, by having a part of the surface thereof mirrored and another part non-mirrored and can be used to adjust the optical sample path length by positioning of the sample carrier.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein:

FIG. 8 shows an embodiment of a device according to this disclosure, comprising an open measurement space;

FIG. 12 is a top view of FIG. 11.

DETAILED DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of the present invention.

Figure 1:
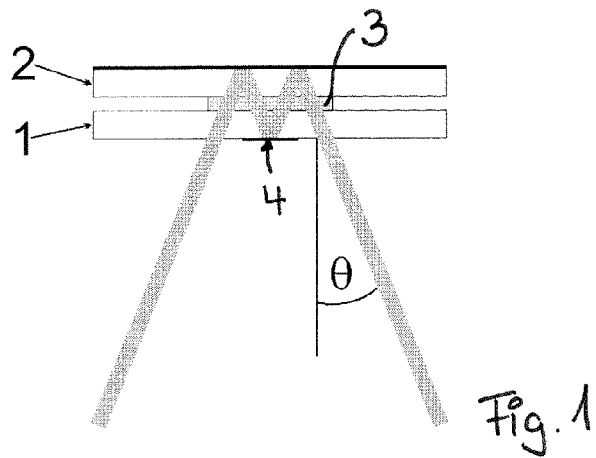
FIG. 1 shows an example of a possible beam path through a measurement space.

FIG. 1 is a schematic illustration of a possible beam path through a measurement space of a device for the analysis of a liquid sample by way of light. The measurement space is delimited by a transparent sample carrier 1 and an upper mirror 2 arranged thereabove. A liquid sample 3 to be analyzed is enclosed between the upper mirror 2 and the sample carrier 1.

In the beam path shown, measurement light is irradiated at an oblique angle of incidence $\theta$, for example 10° to 40° relative to a surface normal of the sample carrier 1, through the sample carrier 1, and then impinges obliquely on the upper mirror 2 arranged parallel to the sample carrier 1. The measurement light beam is reflected by the upper mirror 2 to a lower mirror 4 and from there back to the upper mirror 2. After the second reflection by the upper mirror 2, the measurement light beam runs laterally past the lower mirror 4 and exits the measurement space. The measurement light beam thus passes through the sample a total of four times between the light entrance into the measurement space and the light exit out of the measurement space.

Figure 2:
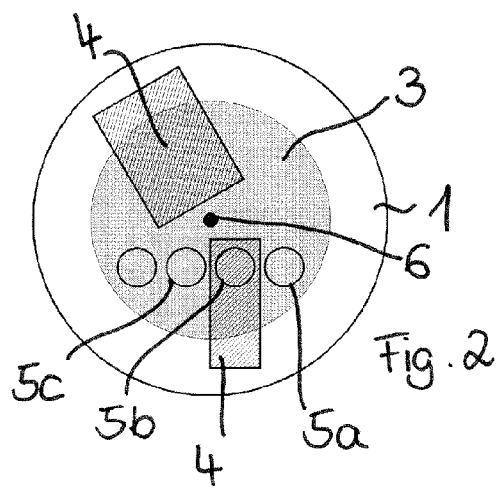
FIG. 2 is a schematic illustration of an illustrative embodiment comprising a lower mirror so as to generate the beam path according to FIG. 1.

FIG. 2 is a schematic illustration of a possible embodiment so as to generate the beam path shown in FIG. 1 in a top view onto the sample carrier 1. The sample carrier 1 containing a sample 3 thereon is mirrored in some regions of the lower face thereof. The mirrored regions of the sample carrier 1 form lower mirrors 4. Upper mirrors 4 and lower mirrors 4 can thus be designed as mirrored glass panels, respectively.

FIG. 2 shows cross-sections of the possible beam path at the angle of incidence $\theta$ as circles 5a, 5b, 5c and 5d. The position of the light entrance is indicated by circle 5a. Another circle 5b indicates where the measurement light beam impinges on the lower mirror 4 after being reflected by the upper mirror 2. A circle 5c next to that marks the light exit of the measurement light beam out of the measurement space for the beam path shown in FIG. 1.

In the embodiment shown, the sample carrier 1 can be rotated, so that the position of the lower mirror 4 relative to the light entrance 5a can be modified. For illustration purposes, FIG. 2 also shows the position of the geometric rotational axis 6 about which the sample carrier 1 can be rotatably moved. Instead of a rotatably movable sample carrier 1 and rotatably movable lower mirrors 4, adjustability of the position of the lower mirror 4 can also be achieved, for example, by displacing the sample carrier 1 or the lower mirror 4 in a linear manner and mounting the same accordingly.

Figure 3:
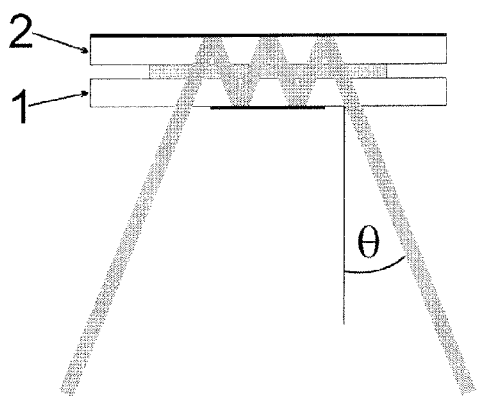
FIG. 3 shows the illustrative embodiment of FIG. 2 in a modified position of the lower mirror.

FIG. 3 shows a representation according to FIG. 2 after a movement of the sample carrier 1. The movement of the sample carrier 1 changed the position of the lower mirror 4 relative to the light entrance 5a. The smaller of the two lower mirrors 4 has been moved out of the first, active position thereof shown in FIG. 2 into a second, inactive position, in which this mirror no longer influences the beam path. The larger lower mirror 4 has been moved out of an inactive position into an active position, in which this mirror reflects a measurement beam path twice back to the upper mirror 2.

Figure 4:
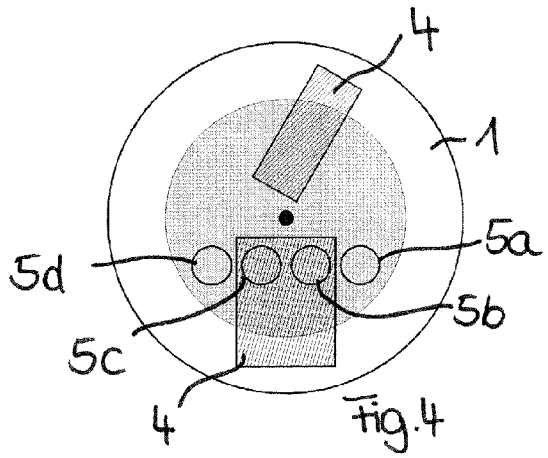
FIG. 4 shows the beam path of FIG. 3.

After the first reflection by the upper mirror 2, the measurement light beam impinges on the area of the lower mirror 4 marked by the circle 5b; after the second reflection, it impinges on the area marked by the circle 5c. After another reflection by the upper mirror 2, the measurement light beam passes the lower mirror 4 and reaches the light exit 5d. FIG. 4 shows the associated beam path in a corresponding sectional view.

For the beam path of FIG. 3, the lower mirror 4 thus brings about a total of six passes of the measurement light beam through the sample 3. This means a 50% increase in the optical sample path length as compared to the position of the lower mirror 4 of FIG. 2, where a total of four passes of the measurement light beam through the measurement space are obtained.

Figure 5:
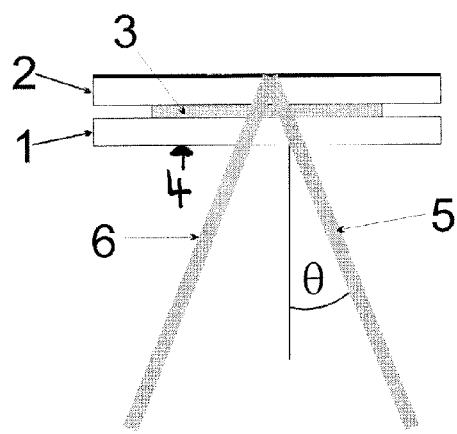
FIG. 5 shows another example of a possible beam path.
Figure 6:
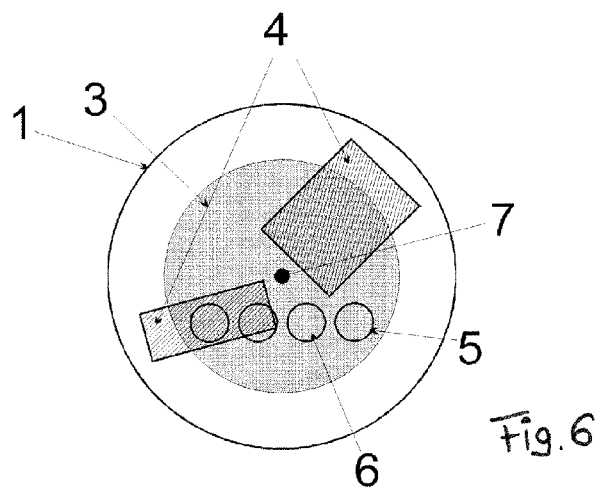
FIG. 6 shows the embodiment of FIG. 2 in a modified position of the lower mirror so as to generate a beam path according to FIG. 5.

FIG. 5 shows another embodiment of a possible beam path. In the beam path shown in FIG. 5, from the light entrance 5a, a measurement light beam reaches the light exit 5b after only a single reflection at the upper mirror 2 and thus exits the measurement space after only two passes through the sample. The beam path shown in FIG. 5 can be achieved by positioning the lower mirrors 4 as shown in FIG. 6. In the arrangement shown in FIG. 6, all lower mirrors 4 are in inactive positions and thus do not influence the beam path.

Figure 7:
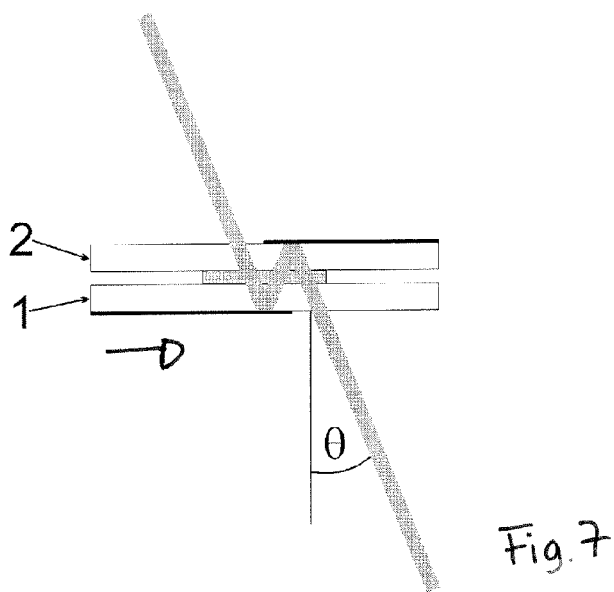
FIG. 7 shows an example of a possible beam path through the measurement space of another embodiment.

In the embodiment described above, the light entrance and light exit in each case take place through the transparent sample carrier 1. This means that a light source and a light detector can be arranged on the same side of the measurement space. FIG. 7 shows a possible beam path of a modified embodiment, in which only the light entrance takes place through the transparent sample carrier 1. In contrast, the light exit takes place through the upper side of the measurement space.

In the embodiment shown in FIG. 7, the lower mirror 4 and upper mirror 2 are each designed as regions of a glass panel that are mirrored. So as to increase the number of passes through the sample, the transparent sample carrier 1 is displaced parallel to the upper mirror 2 in the direction of the arrow shown in FIG. 7. The overlapping region between the upper and lower mirrors is thus enlarged, whereby the number of reflections is increased accordingly.

After having illustrated the basic principle of a device that allows the optical sample path length to be adjusted based on FIGS. 1 to 7, an embodiment of such a device will be described in more detail hereafter with reference to FIGS. 8 to 12.

FIG. 8 shows an embodiment of a device for the analysis of a liquid sample by way of light. The device comprises a stage 10. A transparent sample carrier 1 comprising one or more lower mirrors 4 is arranged in a cut-out of the stage 10. A cover 11, which holds an upper mirror carrier 14 including an upper mirror 2, is pivotably attached to the stage 10.

In FIG. 8, the cover 11, together with the upper minor carrier 14, is folded up, so that the sample carrier 1 can be accessed, for example so as to apply a liquid sample to the sample carrier 1 or remove such a sample therefrom. When the cover 11 is folded from the open position shown in FIG. 8 downward into the closed position thereof, as is shown in FIG. 9, a measurement space forms between the transparent sample carrier 1 and the upper mirror 2, as is shown schematically in FIG. 1.

A housing 12, in which measurement light can be guided to the transparent sample carrier 1, adjoins on the lower face of the stage 10. A suitable measurement light source, for example an LED, can be arranged in this housing 12. In the embodiment shown, additionally a light detector is arranged on the lower face of the stage 10 so as to measure measurement light exiting the measurement space.

Figure 11:
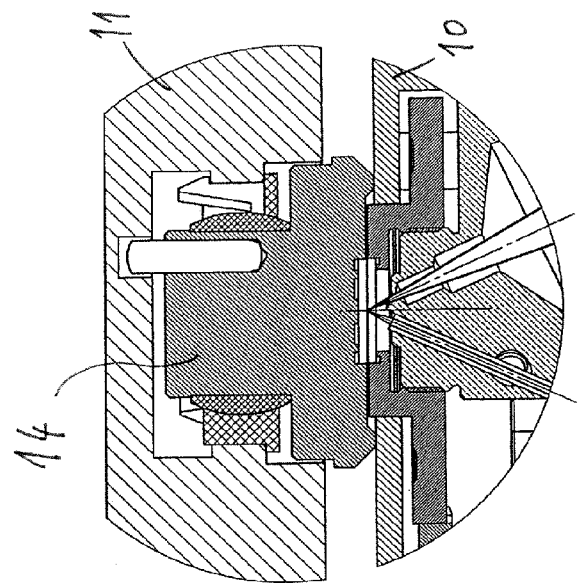
FIG. 11 is an enlarged detailed view of FIG. 10.
Figure 10:
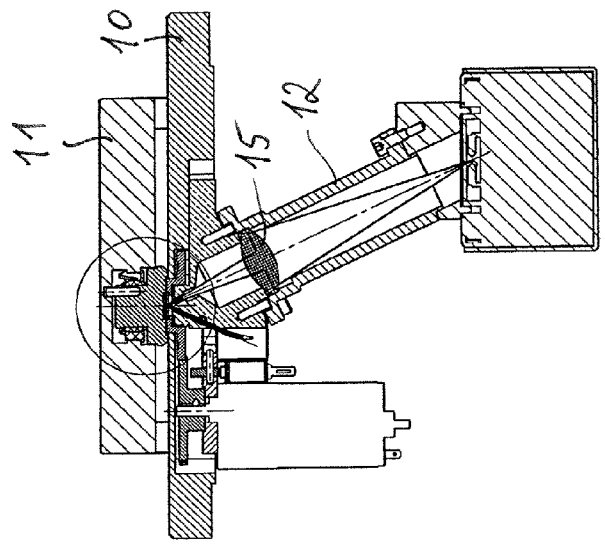
FIG. 10 a sectional view of FIG. 9 along the intersecting line BB.
Figure 9:
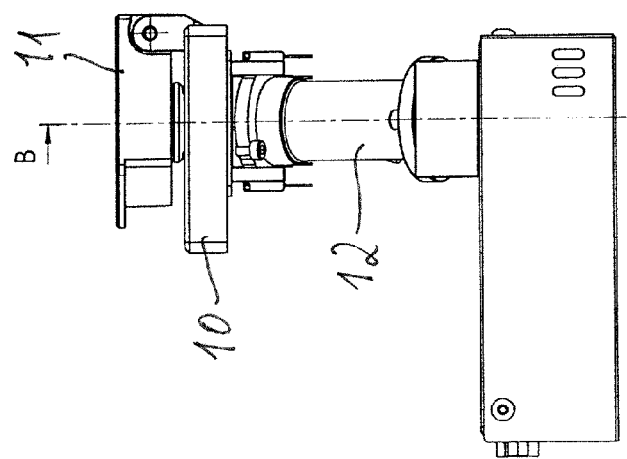
FIG. 9 is a side view of the embodiment with the measurement space closed.

FIG. 10 shows a sectional view along the intersecting line BB of FIG. 9. FIG. 11 shows an enlarged detailed view of FIG. 10. It shows the beam path for measurement light toward the sample carrier 1 and away therefrom. Optical components, for example one or more lenses 15, mirrors or diaphragms can be arranged in the housing 12 so as to define the desired beam path for the oblique incidence of measurement light.

In the device shown, the height of the sample carrier 1 that is arranged in a cut-out of the stage 10 can be adjusted. Preferably an electric motor is provided for adjusting the height. FIG. 11 shows in particular that, in the closed position, the upper mirror carrier 14 is supported on the stage 10. The upper mirror carrier 14 comprises a raised edge for this purpose, which surrounds the upper mirror 2 and can thus be seated on the stage. By displacing the sample carrier 1, the distance between the upper mirror and the sample carrier 1 can thus be adjusted to a desired value.

FIG. 12 shows an enlarged detail of the cut-out of the stage 10 in which the sample carrier 1 is arranged. FIG. 12 also illustrates the beam path of incident and exiting measurement light. It is apparent in particular that a diaphragm part 13 is arranged beneath the sample carrier 1, this part comprising a first opening for measurement light going to the sample carrier 1 and a second opening for measurement light coming from the sample carrier 1. The second opening is considerably larger than the first opening, so that measurement light can pass the opening of the diaphragm part 13, regardless of the number of reflections by the upper mirror 2. This means that a measurement light beam can pass the opening from any of the positions 5a, 5c and 5d that are shown in FIG. 2, if the lower mirror 4 is appropriately positioned. The diaphragm part 13 contains a ridge 13a between the two openings so as to reduce stray light.

While exemplary embodiments have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

REFERENCE NUMERALS 1 sample carrier
2 upper mirror
3 liquid sample
4 lower mirror
5a light entrance
5b possible beam path cross-section
5c possible beam path cross-section
5d possible beam path cross-section
10 sample stage
11 cover
12 housing
13 diaphragm part
13a ridge
14 upper mirror carrier
15 lens

What is claimed is:

1. A device for the photometric analysis of a liquid sample, comprising:
   a transparent sample carrier;
   a movable upper mirror, which can be moved between a closed position, in which the mirror encloses a measurement space between itself and the sample carrier, and an open position, in which the sample carrier can be accessed to apply a sample; and
   a beam path, which guides incident measurement light between a light entrance into the measurement space and a light exit out of the measurement space;
   wherein the beam path guides measurement light at an oblique angle of incidence through the sample carrier to the upper mirror, and further wherein the height of the sample carrier relative to the upper mirror can be adjusted.

2. The device according to claim 1, further comprising a lower mirror to reflect measurement light coming from the upper mirror.

3. The device according to claim 2, wherein the lower mirror can be moved between first and second positions, wherein in the first position the lower mirror causes a larger number of passes of the measurement light beam through the measurement space than in the second position.

4. The device according to claim 2, wherein the lower mirror comprises a mirrored sub-area of the sample carrier.

5. A device according to claim 2, wherein the lower mirror is rotatable.

6. A device according to claim 2, wherein the lower mirror comprises a plurality of lower mirrors arranged at a distance from one another, wherein the number of passes of a measurement light beam through the measurement space brought about by the lower mirrors in their first positions, respectively, is different.

7. A device according to claim 2, wherein the sample carrier is arranged in a cut-out of a sample carrier stage.

8. A device according to claim 2, further comprising a diaphragm part arranged beneath the sample carrier, the diaphragm part comprising an entrance diaphragm and an exit diaphragm.

9. The device according to claim 8, wherein the exit diaphragm has a larger passage area than the entrance diaphragm.

10. The device according to claim 8, wherein the diaphragm part comprises a ridge between the two diaphragms.

11. A device according to claim 1, wherein the upper mirror is held by a mirror carrier, which is attached to a cover that is pivotably mounted on a stage.

12. The device according to claim 11, wherein the mirror carrier comprises a raised edge that surrounds the upper mirror.

13. The device according to claim 11, wherein the upper mirror carrier is seated on the stage when the upper mirror covers the sample carrier.

14. A device for the photometric analysis of a liquid sample, comprising:
   a transparent sample carrier;
   a movable upper mirror, which can be moved between a closed position, in which the mirror encloses a measurement space between itself and the sample carrier, and an open position, in which the sample carrier can be accessed to apply a sample;
   a beam path, which guides incident measurement light between a light entrance into the measurement space and a light exit out of the measurement space, wherein the beam path guides measurement light at an oblique angle of incidence through the sample carrier to the upper mirror; and
   a lower mirror configured to reflect measurement light coming from the upper mirror, the lower mirror being movable between first and second positions, wherein in the first position the lower mirror causes a larger number of passes of the measurement light beam through the measurement space than in the second position.

15. A device for the photometric analysis of a liquid sample, comprising:
   a transparent sample carrier;
   a movable upper mirror, which can be moved between a closed position, in which the mirror encloses a measurement space between itself and the sample carrier, and an open position, in which the sample carrier can be accessed to apply a sample;
   a beam path, which guides incident measurement light between a light entrance into the measurement space and a light exit out of the measurement space, wherein the beam path guides measurement light at an oblique angle of incidence through the sample carrier to the upper mirror; and
   a lower mirror configured to reflect measurement light coming from the upper mirror, the lower mirror being rotatable.

* * * * *